(12) United States Patent
Chen et al.

(10) Patent No.: US 7,777,060 B2
(45) Date of Patent: Aug. 17, 2010

(54) PLATINUM ANALOGS WITH BIS-NITRILE-CONTAINING LIGANDS

(75) Inventors: Xinghai Chen, San Antonio, TX (US); Pavankumar N. V. Petluru, San Antonio, TX (US); Qiuli Huang, San Antonio, TX (US); Kesavaram Narkunan, San Antonio, TX (US); Frederick Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 11/978,818

(22) Filed: Oct. 30, 2007

(65) Prior Publication Data

US 2008/0194680 A1      Aug. 14, 2008

Related U.S. Application Data

(60) Provisional application No. 60/901,190, filed on Feb. 14, 2007.

(51) Int. Cl.
*C07F 15/00* (2006.01)
*A61K 31/282* (2006.01)
*A61P 35/00* (2006.01)

(52) U.S. Cl. .................. 556/137; 514/184; 514/450; 514/492; 514/579

(58) Field of Classification Search ............... None
See application file for complete search history.

(56) References Cited

U.S. PATENT DOCUMENTS 7,238,823 B2 *   7/2007   Xiao et al. ............... 556/137

OTHER PUBLICATIONS

Kukushkin et al., Cis-bis (benzeneacetonitrile)dichloroplatinum (II) and trans-bis(benzeneacetonitrile)dichloroplatinum(II), Inorganic Syntheses, 1998, vol. 32, pp. 144-148.*

* cited by examiner

*Primary Examiner*—Rosalynd Keys
(74) *Attorney, Agent, or Firm*—Scott A. Whitaker

(57) ABSTRACT

Disclosed herein are novel platinum-based analogs possessing two nitrile substituent groups (bis-nitrile) covalently-bonded to the platinum. Also disclosed herein are the reaction schemes for the synthesis of said platinum complexes, as well as quantitative in vitro IC50 data.

4 Claims, No Drawings

PLATINUM ANALOGS WITH BIS-NITRILE-CONTAINING LIGANDS

RELATED APPLICATIONS

The present application claims priority to Provisional Application Ser. No. 60/901,190 filed Feb. 14, 2007 and entitled: "PLATINUM ANALOGS WITH BIS-NITRILE-CONTAINING LIGANDS".

FIELD OF THE INVENTION

The present invention relates to novel platinum complexes possessing bis-nitrile-containing ligands and derivatives thereof, as well as methods for the synthesis of these aforementioned platinum complexes and derivatives thereof.

BACKGROUND OF THE INVENTION

The antineoplastic drug cisplatin(cis-diaminedichloroplatinum (II) or "CDDP"), and related platinum based drugs including carboplatin and oxaliplatin, are widely used in the treatment of a variety of malignancies, including, but not limited to, cancers of the ovary, lung, colon, bladder, germ cell tumors and head and neck. Platinum analogs are reported to act, in part, by aquation to form reactive aqua species (Scheme 1), some of which may predominate intracellularly, and subsequently form DNA intrastrand adducts with purine bases (predominantly intrastrand adducts between adjacent purine bases and less commonly as interstrand crosslinks between purine bases) and disrupting the DNA structure and function, which is cytotoxic to cancer cells.

Scheme 1

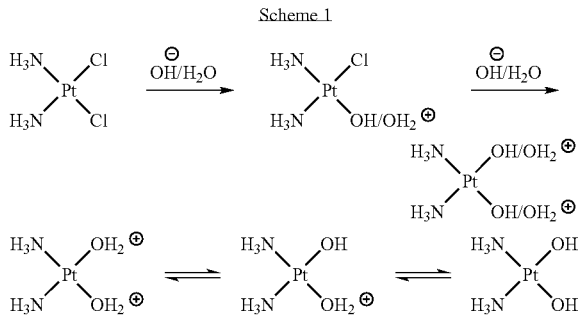

Cisplatin is relatively stable in human plasma, where a high concentration of chloride prevents aquation of cisplatin. Once cisplatin enters a tumor cell, where a much lower concentration of chloride exists, one or both of the chloride ligands of cisplatin is displaced by water to form a reactive aqua intermediate (as illustrated above), which in turn can react rapidly with DNA purines to form stable platinum-purine DNA adducts.

The postulated anti-tumor mechanisms of action of cisplatin-like agents is achieved by: (i) attacking the cellular DNA and forming intra- and inter-strand adducts; (ii) the $N_7$ of Guanine (G) is the primary site of attack, followed by the $N_7$ of Adenine (A); and (iii) the majority of adducts are of the intra-strand type with 60-70% being 1,2-GG intra-strand adducts, ~30% being 1,2-AG intra-strand adducts, and ~10% being 1,3-GG intra-strand adducts and ~2% of 1,2-GG inter-strand crosslinks.

As mentioned above, many cancers exhibit varying degrees of cytotoxic sensitivity to platinum drugs, as evidenced by tumor regression following initial treatment, but subsequently develop increasing levels of platinum resistance which is manifested as an absence of tumor shrinkage or by tumor growth progression or metastases during or following treatment with the platinum drug (i.e., "acquired resistance").

An unwanted side reaction of platinum species is the reactions with physiological thiols and disulfides as well as proteins; such reactions are thought to be not beneficial in killing tumor cells because these reactions inactivate the platinum species thereby leading to platinum-resistant cancer cells.

Therefore, the development of platinum compounds that do not react as readily with physiological thiols/disulfides and proteins may be markedly more effective against platinum-resistant tumors than either cisplatin or the currently utilized compounds. New platinum agents are sought which can effectively kill tumor cells but that are also insensitive or less susceptible to tumor-mediated drug resistance mechanisms that are observed with other platinum agents.

In an attempt to solve this problem, we have been developing nitrile-based platinum derivatives which have shown better activity not only in the wild type cancer cells but also in cisplatin and oxaliplatin resistant cell lines. The structural formula for this analog is shown below:

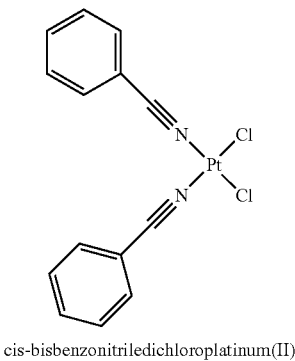

cis-bisbenzonitriledichloroplatinum(II)

In general, nitrile-ligand based platinum complexes are less polar and are more hydrophobic (i.e., water repelling) than the currently-marketed platinum-based drugs, and thus can be dissolved into less polar solvents including, but not limited to, methylene dichloride, dimethylacetamide (DMA), and the like. This greater lipophilicity may allow such analogs to be taken up more readily by cancer cells, by facile diffusion/transport through the lipid bilayer of the cell membrane, than current drugs, thereby increasing the available concentration of the platinum species that can participate in cytotoxic anti-tumor effects on the DNA within cancer cells.

Additionally, the lone pair of electrons on nitrogen in the nitrile group is located in the sp hybrid orbital, which is closer to the nitrogen nucleus than the $sp^3$ hybrid orbital in the ammine ligand in cisplatin. Thus, in bis-nitrile-based platinum analogs, the attraction of the lone pair of electrons on nitrogen with platinum is greater than in the amine ligand and platinum in cisplatin. This effect results in decreasing the ionic effect between platinum(II) and the leaving group thereby increasing the covalent bonding between platinum and the leaving group. As a result, the leaving groups are more difficult to be displaced by substitution, including aquation, and therefore slower rates of aquation may be observed in nitrile-based platinum complexes as compared to ammine platinum complexes.

Slower rates of aquation is equally important from a pharmacological, toxicological, chemical and drug-resistance circumvention mechanistic points of view, by predicting the nitrile-containing platinum complexes described below to be less chemically reactive than cisplatin, carboplatin and oxaliplatin. Therefore, these nitrile-containing platinum complexes react more slowly with, and thereby avoiding unwanted platinum-sulfur and platinum-nitrogen conjugates with, the thiols, disulfides and proteins/peptides present in vivo; specifically the sulfur-containing physiological thiols, disulfides and peptides/amino acids, including but not limited to, glutathione, cysteine, homocysteine, methionine and all other sulfur-containing and imidazole-containing (e.g., histidine), or arginine or lysine di-tri- and larger peptides, that participate in tumor-mediated platinum drug resistance.

Therefore, these novel bis-nitrile-based platinum complexes have potential to circumvent de novo and acquired tumor-mediated cisplatin resistance and kill cancer cells with natural resistance to known platinum drugs. The platinum complexes described below are also thought to permit controlled reduction of the chemical reactivity of the platinum species to such a degree that greater amounts of the platinum species are also delivered intracellularly. This improved delivery of platinum that is available for intracellular DNA adducts formation is mediated by substantial reduction in the amount of non-effective and non-specific reactions of these novel platinum species with proteins and physiological thiols and disulfides, which can attenuate the antitumor effects of conventional platinum analogs.

SUMMARY OF THE INVENTION

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

Disclosed herein are novel platinum-based analogs with a substituted nitrile ligand: RC≡N, wherein the RC≡N functional group is covalently bonded to the platinum. The analogs also have donor ligands capable of forming hydrogen bonds with the bases in DNA or RNA. The reaction scheme for hydrolysis of the leaving groups in these novel platinum-based complexes would be analogous to that shown above for cisplatin, where the intermediates at the leaving group sites include $OH/OH_2^+$; $OH_2^+$ and OH.

In the platinum-based analogs of the present invention, either one or both of the leaving groups will be hydrolyzed in the intracellular environment making the molecule labile and suitable for nucleophilic substitution, as well as leading to adduct formation with the Guanine or Adenine base of a DNA (or possibly also an RNA) oligonucleotide.

These bis-nitrile platinum analogs may also be more easily transported into tumor cells, due to their increased lipophilicity. Hence, these novel analogs are likely to be useful as anti-neoplastic agents, and in modulating or interfering with the synthesis or replication or transcription of DNA or translation or function of RNA in vitro or in vivo, as they are potentially capable of forming a platinum coordinate complex with an intact or nascent DNA or RNA and thereby interfering with cellular synthesis, transcription or replication of nucleic acid polynucleotides.

DETAILED DESCRIPTION OF THE INVENTION

The preferred embodiments herein described are not intended to be exhaustive, or to limit the invention to the precise forms disclosed. They are chosen and described to best illustrate the principles of the invention, and its application and practical use to best enable others skilled in the art to follow its teachings.

DEFINITIONS

"Scaffold" or "Skeleton" means the fixed structural part of the molecule of the formula given.

"Fragments", "Moieties" or "Substituent Groups" are the variable parts of the molecule, designated in the formula by variable symbols, such as $R_x$, X or other symbols. Fragments may consist of one or more of the following:

"$C_x$—$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$—$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$—$C_y$ alkenyl or alkynyl" means a straight or branched chain hydrocarbon with at least one double bond(alkenyl) or triple bond (alkynyl) between two of the carbon atoms;

"$C_x$—$C_y$ alkoxy" means a straight or branched hydrocarbon chain with as few as x and as many as y carbon atoms, with the chain bonded to the scaffold through an oxygen atom;

"Alkoxycarbonyl" (aryloxycarbonyl) means an alkoxy (aryloxy) moiety bonded to the scaffold through a carbonyl;

"Halogen" or "Halo" means chloro, fluoro, bromo or iodo;

"Acyl" means —C(O)—R, where R is hydrogen, $C_x$—$C_y$ alkyl, aryl, $C_x$—$C_y$ alkenyl, $C_x$—$C_y$ alkynyl, and the like;

"Acyloxy" means —O—C(O)—R, where R is hydrogen, $C_x$—$C_y$ alkyl, aryl, and the like;

"$C_x$—$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic analogs of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contain from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Azide" means any group of analogs having the characteristic formula $R(N_3)x$. R may be almost any metal atom, a hydrogen atom, a halogen atom, the ammonium radical, a complex $[CO(NH_3)_6]$, $[Hg(CN)_2M]$, (with M=Cu, Zn, Co, Ni) an organic radical like methyl, phenyl, nitrophenol, dinitrophenol, p-nitrobenzyl, ethyl nitrate, and the like. The azide group possesses a chain structure rather than a ring structure;

As used herein the term "bis", is a prefix meaning twice or again. Used in chemical nomenclature to indicate that a chemical grouping or radical occurs twice within a molecule, e.g., bisphenol A, where two phenolic groups are found: $(CH_3)_2C(C_6H_5OH)_2$.

"Imine" means a class of nitrogen-containing analogs possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

As used herein, the term "Leaving Group" is a group which can be replaced by a nucleophile or other functional group and in the present invention the leaving groups are chloride groups (Cl⁻).

As used herein the term "Nitrile" means an organic compound containing the —C≡N grouping.

As used herein, the term "Substituted" modifies the identified fragments (moieties) by replacing any, some or all of the hydrogen atoms with a moiety (moieties) as identified in the specification. Substitutions for hydrogen atoms to form substituted analogs include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

The term "antineoplastic agent" or "chemotherapeutic agent" refers to an agent that inhibits, prevents, or stops the growth or metastases of neoplasms, or kills neoplastic cells directly by necrosis, or by apoptosis of neoplasms.

As used herein, the term "$IC_{50}$" represents the half maximal inhibitory concentration of an inhibitor that is required for 50% inhibition of, e.g., enzymes, cells, cellular receptors, or microorganisms. $IC_{50}$ values are dependent upon the conditions under which they are measured. The $IC_{50}$ is commonly utilized as a measure of drug effectiveness. According to the FDA, $IC_{50}$ represents the concentration of a drug that is required for 50% inhibition in vitro.

As defined in the present invention, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be prevention, mitigation, reduction in severity, shortening the time to resolution or alleviation of the signs, symptoms, or exert a medically-beneficial effect upon the underlying pathophysiology or pathogenesis of an expected or observed side-effect, toxicity, disorder or condition, or any other desired alteration of a biological system. In the present invention, the result will generally include the prevention, delay, mitigation, decrease, or reversal of chemotherapeutic agent-associated toxicity, and an increase in the frequency, number or treatments and/or duration of chemotherapeutic therapy.

As used herein, "preventing" means preventing the onset, or the development of greater severity in an adverse sign or condition in a subject, in whole or in-part, or ameliorating or controlling such adverse sign or condition in the subject, as they involve any such chemotherapeutic agent-associated adverse side effect.

I. Synthetic Procedures for the Bis-Nitrile Compounds of the Present Invention

It should be noted that following the IUPAC nomenclature, the term "BNPxxxx", refers to the BioNumerik Pharmaceuticals, Inc., in-house BNP number which serve to allow rapid identification of the various compounds. These BNP numbers are also utilized for identification in the following Table 1, infra.

Cis-(3-[2-(2-cyano-ethoxy)-ethoxy]-propionitrile) dichloroplatinum (II) (BNP 3015)

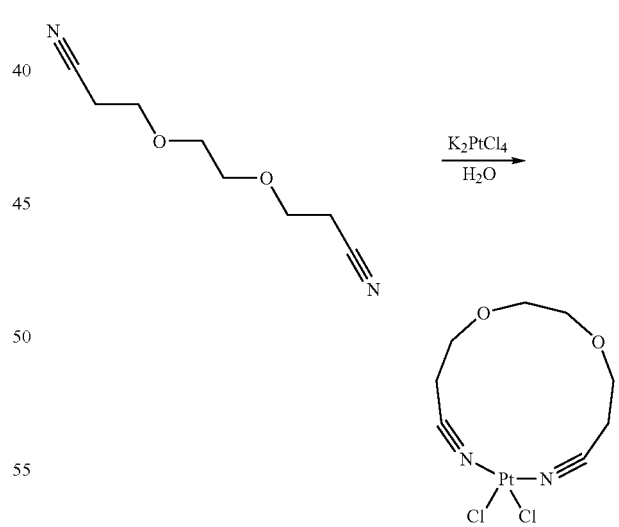

To a solution of potassium tetrachloroplatinate (500 mg, 1.2 mmol) in deionized water (5 mL), 3-[2-(2-cyano-ethoxy)-ethoxy]-propionitrile (203 mg, 1.2 mmol) was added and stirred at room temperature for 4 days. The reaction mixture was extracted with diethyl ether (3-times with 20 mL) and was filtered on a Buckner flask. Solids were washed sequentially with water and ether, and finally dried under vacuum to yield the designed product.

¹H NMR (DMF-d7, 300 MHz): δ 3.82-3.76 (m, 4H), 3.64 (s, 2H), 3.27-3.15 (m, 6H); ¹⁹⁵Pt (DMF-d7, 64.5 MHz): δ −2244.3

Cis-bis(3-methoxy-propionitrile)dichloroplatinum (II) (BNP 2509)

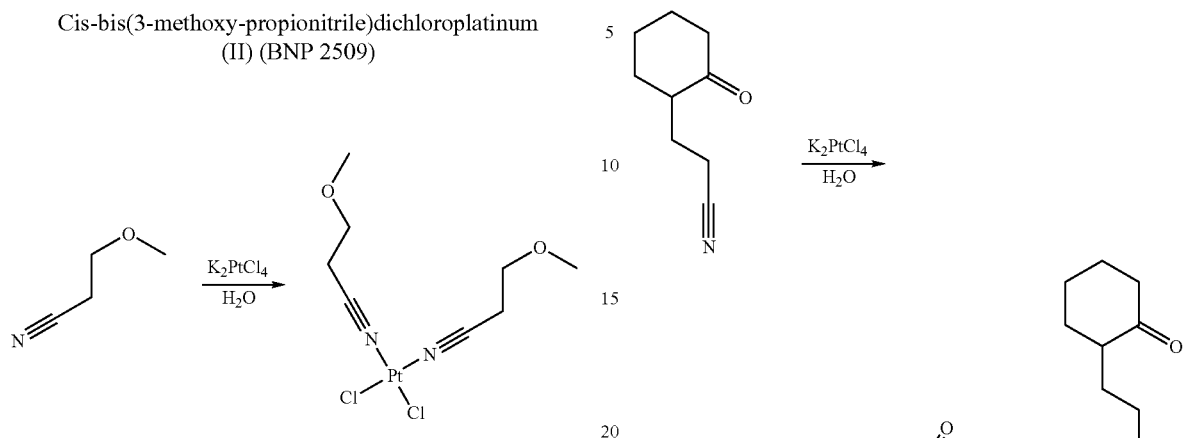

To a solution of potassium tetrachloroplatinate (450 mg, 1.2 mmol) in deionized water (15 mL), 3-methoxy-propionitrile (950 mg, 11.2 mmol) was added and stirred at room temperature for 3 days. The reaction mixture was extracted with diethyl ether (3-times with 20 mL) and was filtered on a Buckner flask. Solids were washed sequentially with water and ether, and finally dried under vacuum to yield the designed product.

¹H NMR (DMF-d7, 300 MHz): δ 3.71 (t, 4H, J=5.7 Hz), 3.54 (t, 4H, J=5.7 Hz), 3.37 (s, 6H). ¹⁹⁵Pt (DMF-d7, 64.5 MHz): δ −2336.8

Cis-bis(morpholine-4-carbonitrile)dichloroplatinum (II) (BNP3019)

To a solution of potassium tetrachloroplatinate (400 mg, 0.96 mmol) in deionized water (5 mL), morpholine-4-carbonitrile (1 mL) was added and stirred at room temperature for 5 hours. The reaction mixture was extracted with diethyl ether (3-times with 20 mL) and was filtered on a Buckner flask. Solids were washed sequentially with water and diethyl ether, and finally dried under vacuum to yield the designed product.

¹H NMR (DMF-d7, 300 MHz): δ 3.79-3.76 (m, 8H), 3.52-3.48 (m, 8H); ¹⁹⁵Pt(DMF-d7, 64.5 MHz): δ −2146.0

Cis-bis[3-(2-oxo-cyclohexyl)-propionitrile]dichloroplatinum (II) (BNP3020)

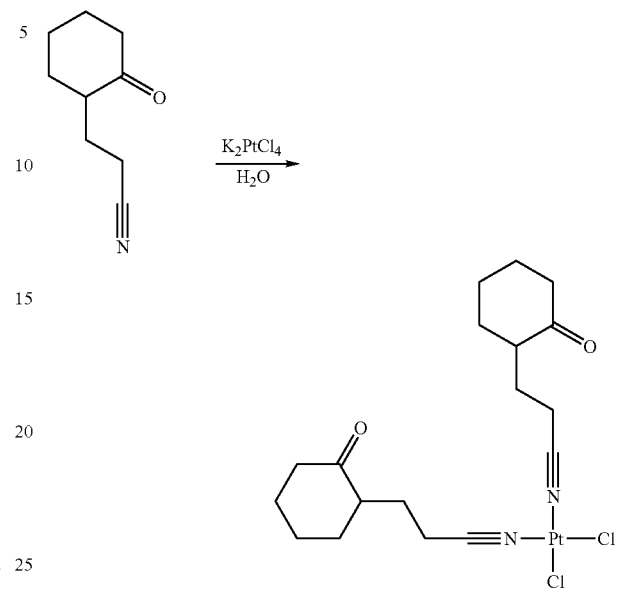

To a solution of potassium tetrachloroplatinate (400 mg, 0.96 mmol) in deionized water (5 mL), 3-(2-oxo-cyclohexyl)-propionitrile (1 g, 6.6 mmol) was added and stirred at room temperature for 16 hours. The reaction mixture was extracted with diethyl ether (20 mL) and was filtered on a Buckner flask. Solids were washed sequentially with water and diethyl ether, crystallized from dichloromethane and diethyl ether, and finally dried under vacuum to yield the designed product.

¹H NMR (DMF-d7, 300 MHz): δ 3.22-3.15 (m, 4H), 2.70-2.58 (m, 2H), 2.54-2.42 (m, 2H), 2.35-2.02 (m, 8H), 1.92-1.54 (m, 8H), 1.46-1.32 (m, 2H); ¹⁹⁵Pt (DMF-d7, 64.5 MHz): δ −2240.7

Cis-bis[(3-fluoro-phenyl)-acetonitrile]dichloroplatinum (II) (BNP3028)

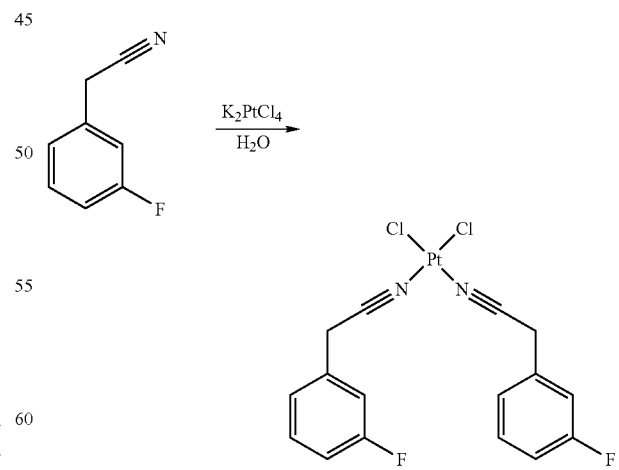

To a solution of potassium tetrachloroplatinate (400 mg, 0.96 mmol) in deionized water (15 mL), (3-fluoro-phenyl)-acetonitrile (1.0 g, 7.4 mmol) was added and stirred at room temperature for 2 days. The reaction mixture was extracted with diethyl ether (3-times with 20 mL) and was filtered on a Buckner flask. Solids were washed sequentially with water and diethyl ether, and finally dried under vacuum to yield the pure designed product.

¹H NMR (DMF-d7, 300 MHz): δ 7.55-7.22 (m, 8H), 3.48 (s, 4H); ¹⁹⁵Pt (DMF-d7, 64.5 MHz): δ −2279.3

Cis-bis(bicyclo[4.2.0]octa-1(6),2,4-triene-7-carbonitrile)dichloroplatinum (II) (BNP3030)

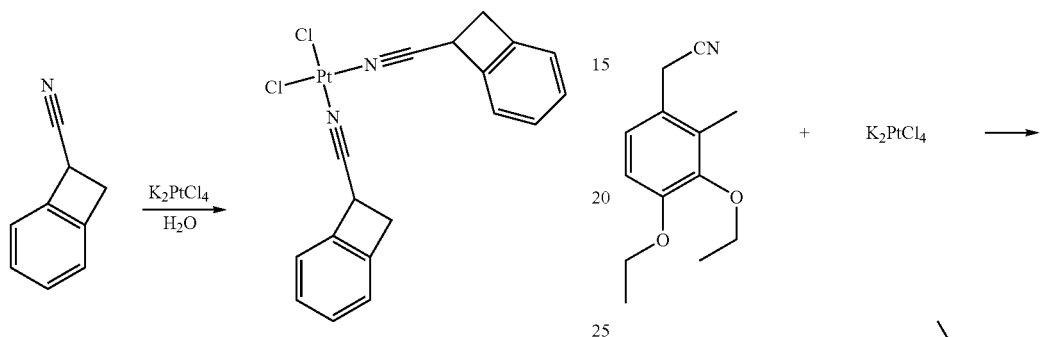

To a solution of potassium tetrachloroplatinate (450 mg, 1.08 mmol) in deionized water (15 mL), bicyclo[4.2.0]octa-1(6),2,4-triene-7-carbonitrile (1.0 g, 7.74 mmol) was added and stirred at room temperature for 3 days. The reaction mixture was extracted with diethyl ether (3-times with 20 mL) and was filtered on a Buckner flask. Solids were washed sequentially with water and diethyl ether, and finally dried under vacuum to yield the pure designed product.

¹H NMR (DMF-d7, 300 MHz): δ 7.45-7.26 (m, 8H), 5.16-5.13 (m, 2H), 3.92-3.62 (m, 4H); ¹⁹⁵Pt (DMF-d7, 64.5 MHz): δ −2257.9

Cis-bis-(o-tolylacetonitrile)dichloroplatinum (II) (BNP3024)

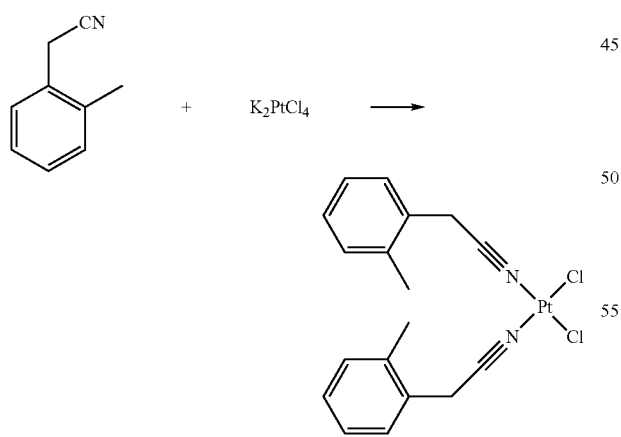

The reaction mixture of o-tolylacetonitrile (1.0 g, 7.6 mmol) and potassium tetrachloroplatinate (0.5 g, 1.2 mmol) in water (5 mL) was stirred vigorously at room temperature for three days. There was gray solid formation in the organic layer. The gray color solid was isolated by filtration, washed with diethyl ether. It was dissolved in dichloromethane and ether was added slowly to the above solution to precipitate the product. The precipitate was isolated by filtration to give 0.24 g of platinum product.

¹H NMR (300 MHz, DMF-d7): δ 7.45-7.30 (m, 8H), 4.68 (s, 4H), 2.39 (s, 6H); ¹⁹⁵Pt (64.4 MHz, DMF-d7): δ −2257.4; MS (M⁺+Na): 552.29.

Cis-bis[3,4-diethoxy-phenyl)acetonitrile]dichloroplatinum (II) (BNP3035)

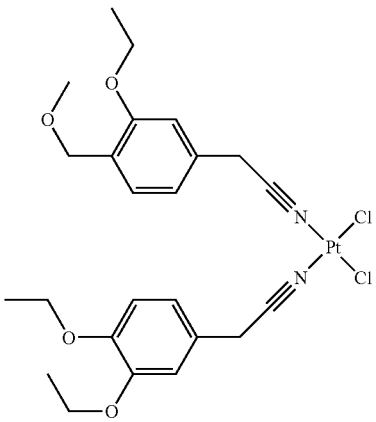

The reaction mixture of 3,4-diethoxy-phenylacetonitrile (0.75 g, 3.6 mmol) and potassium tetrachloroplatinate (0.5 g, 1.2 mmol) in water (5 mL) was heated to 60° C. and stirred vigorously for 24 hours. The formed gray color solid was isolated by filtration, washed in diethyl ether and dichloromethane. 30 mg of the platinum product was obtained.

¹H NMR (300 MHz, DMF-d7): δ 7.10-6.96 (m, 6H), 4.69 (s, 4H), 4.08 (m, 8H), 1.35 (m, 12H); ¹⁹⁵Pt NMR (64.4 MHz, DMF-d7): δ −1985.1.

Trans-bis(2,6-difluoro-3-methylphenylacetonitrile)dichloroplatinum (II) (BNP3036/t)

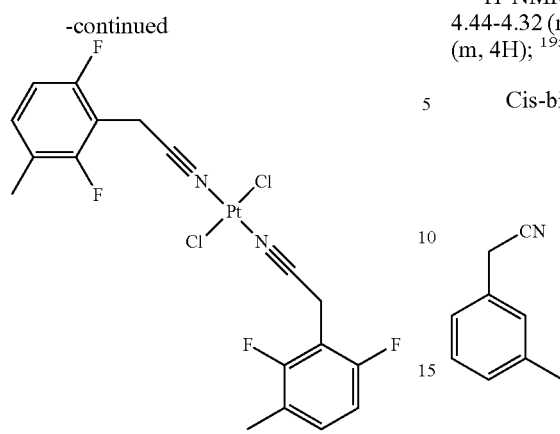

The reaction mixture of 2,6-difluoro-3-methylphenylacetonitrile (0.68 g, 4.1 mmol) and potassium tetrachloroplatinate (0.5 g, 1.2 mmol) in water (5 mL) was heated to 90° C. and stirred vigorously for 48 hours. Gray solid precipitated from the reaction mixture. The supernatant was removed with a pipette. The remaining residue was washed with ether. The gray color solid was isolated by filtration. The isolated solid was dissolved in dichloromethane and allowed the solvent to evaporate slowly until a small amount of solution remained. Light green color needle shape crystal formed along with the evaporation of solvent. It was isolated to give 0.18 g of platinum product.

$^1$H NMR (300 MHz, DMF-d7): δ 7.45 (m, 2H), 7.13 (m, 2H), 4.86 (s, 4H), 2.64 (s, 6H); $^{195}$Pt NMR (64.4 MHz, DMF-d7): δ −2369.5.

Cis-bis(4-methoxy-4-phenylbutyronitrile)dichloroplatinum (II) (BNP3017)

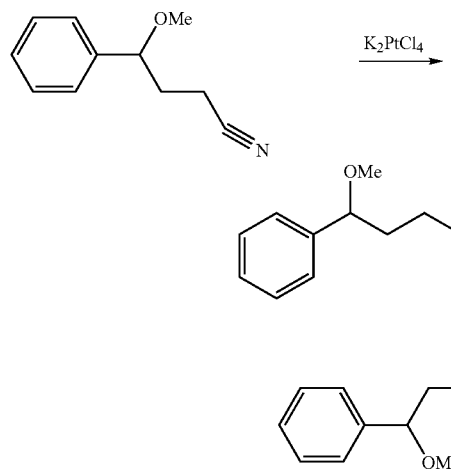

To a solution of potassium tetrachloroplatinate (415 mg, 1 mmol) in deionized water (3 mL), 4-methoxy-4-phenylbutyronitrile (800 mg, 4.6 mmol) was introduced dropwise and stirred under argon at room temperature for 6 days. The reaction mixture was diluted with water (5 mL) and ether (10 mL), stirred vigorously for 10 minuets, and filtered on a Buckner flask. Solids were washed sequentially with ether (10 mL) and water (10 mL) and finally dried under vacuum for 12 hours to yield 250 mg of the required product.

$^1$H NMR (DMF-d7, 300 MHz): δ 7.50-7.22 (m, 10H), 4.44-4.32 (m, 2H), 3.23 (s, 6H), 3.32-3.10 (m, 4H), 2.20-2.00 (m, 4H); $^{195}$Pt (DMF-d7, 64.5 MHz): δ −2239.3.

Cis-bis(m-tolylacetonitrile)dichloroplatinum (II) (BNP3026)

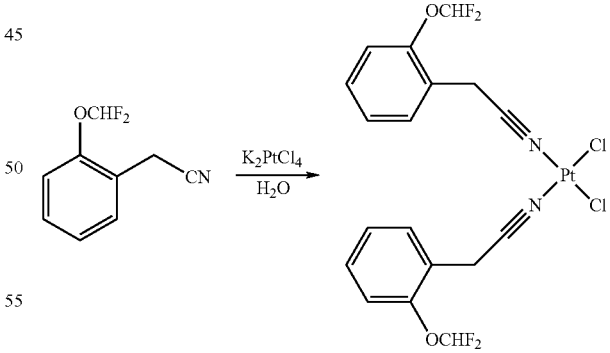

To a solution of potassium tetrachloroplatinate (415 mg, 1 mmol) in deionized water (3 mL), m-tolylacetonitrile (660 mg, 5 mmol) was introduced dropwise and stirred under argon at room temperature for 5 days. The reaction mixture was diluted with water (5 mL) and ether (10 mL), stirred vigorously for 10 minuets, and filtered on a Buckner flask. Solids were washed sequentially with ether (10 mL) and water (10 mL), and finally dried under vacuum for 12 hours to yield 193 mg of the required product.

$^1$H NMR (CDCl$_3$, 300 MHz): δ 7.26-7.00 (m, 8H), 4.11 (s, 4H), 2.32 (s, 6H); $^{195}$Pt(CDCl$_3$, 64.5 MHz): δ −2280.8

Cis-bis[2-(difluoromethoxy)phenylacetonitrile]dichloroplatinum (II) (BNP3038)

To a solution of potassium tetrachloroplatinate (415 mg, 1 mmol) in deionized water (3 mL), 2-(difluoromethoxy)phenylacetonitrile (735 mg, 5 mmol) was introduced dropwise and stirred under argon at room temperature for 8 days. The reaction mixture was diluted with water (5 mL) and ether (10 mL), stirred vigorously for 10 minuets, and filtered on a Buckner flask. Solids were washed sequentially with ether (10 mL) and water (10 mL), and finally dried under vacuum for 12 hours to yield 50 mg of the required product.

$^1$H NMR (CDCl$_3$, 300 MHz): δ 7.50-7.10 (m, 8H), 6.65 (t, J=72.6 Hz, 2H), 4.17 (s, 4H); $^{195}$Pt(CDCl$_3$, 64.5 MHz): δ −2297.1

Cis-bis(4-methyl-4 nitro-veleronitrile)dichloroplatinum (II) (BNP3018)

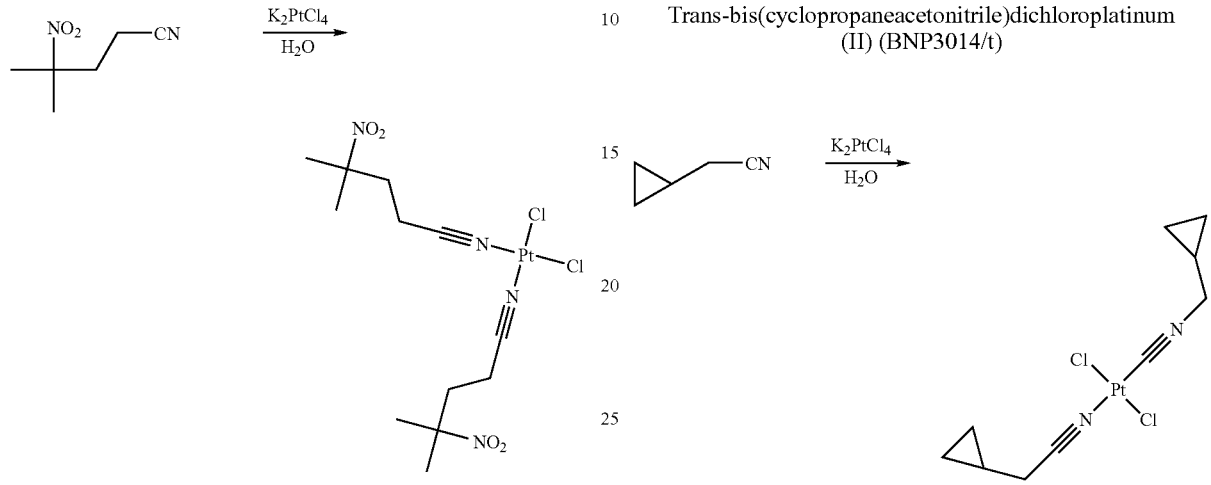

A mixture of potassium tetrachloroplatinate (415 mg, 1.0 mmol) and 4-methy-4-nitroveleronitrile (4 mmol) in deionized water was stirred for 3 days at room temperature. The reaction mixture was extracted with diethyl ether (3-times with 20 mL) and was filtered on a Buckner flask. Solids were washed sequentially with water and ether, which was further purified by recrystallization to yield the pure product (180 mg).
$^1$H-NMR (300 MHz, CDCl$_3$): δ 3.05 (t, J=7.5 Hz, 4H), 2.50 (t, J=7.5 Hz, 4H), 1.68 (s, 12H); $^{195}$Pt NMR (64.5 MHz, CDCl$_3$): δ −2294.

Cis-bis(3-butoxypropanenitrile)dichloroplatinum (II) (BNP3022)

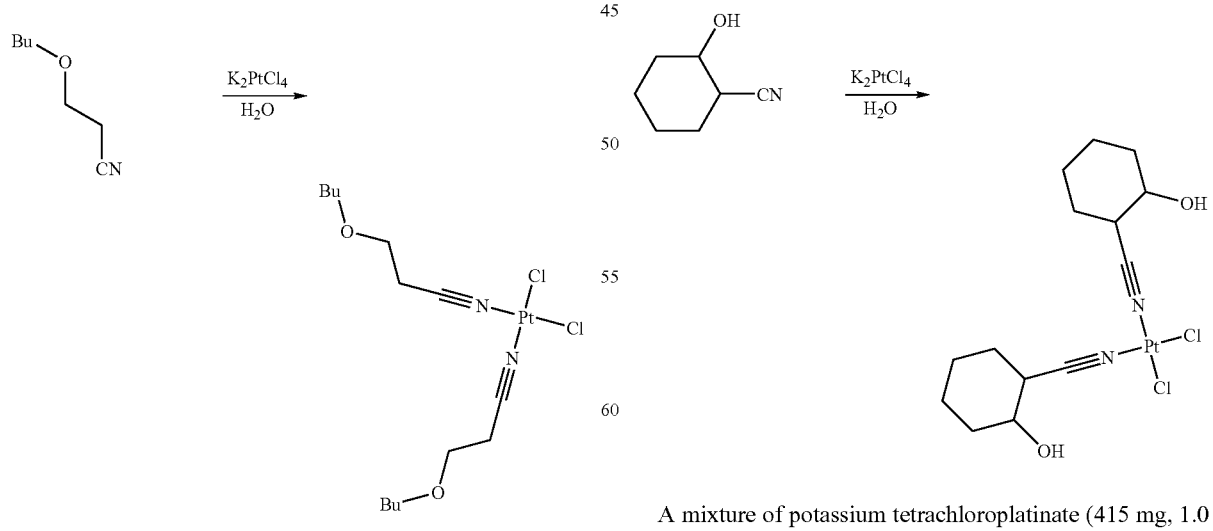

A mixture of potassium tetrachloroplatinate (415 mg, 1.0 mmol) and 3-butoxypropanenitrile (10 mmol) in deionized water was stirred for 5 days at 60° C. The aqueous solution was lyophilized to give a yellow solid, which was further purified by recrystallization to yield the pure product (120 mg).
$^1$H-NMR (300 MHz, CDCl$_3$): δ 3.70 (t, J=6.3 Hz, 4H), 3.50 (t, J=6.3 Hz, 4H), 3.05 (t, J=6.3 Hz, 4H), 1.55-1.60 (m, 4H), 1.30-1.45 (m, 4H), 0.93 (t, J=7.2 Hz, 6H); $^{195}$Pt NMR(64.5 MHz, CDCl$_3$): δ −2294.3.

Trans-bis(cyclopropaneacetonitrile)dichloroplatinum (II) (BNP3014/t)

A mixture of potassium tetrachloroplatinate (415 mg, 1.0 mmol) and cyclopropaneacetonitrile (5 mmol) in deionized water was stirred for 6 hours at 65° C. The reaction mixture was extracted with diethyl ether (3-times with 20 mL) and was filtered on a Buckner flask. Solids were washed sequentially with water and ether, which was further purified by recrystallization to yield the pure product (250 mg).
$^1$H-NMR (300 MHz, CDCl$_3$): δ 2.86-2.82 (m, 4H), 1.22-1.14 (m, 2H), 0.78-0.72 (m, 4H), 0.44-0.38 (m, 4H); $^{195}$Pt NMR (64.5 MHz, CDCl$_3$): δ −2340.0.

Cis-bis(2-hydroxycyclohexanecarbonitrile)dichloroplatinum (II) (BNP3013)

A mixture of potassium tetrachloroplatinate (415 mg, 1.0 mmol) and 2-hydroxycyclohexanecarbonitrile (4 mmol) in deionized water was stirred for 1 day at room temperature. The reaction mixture was extracted with diethyl ether (3-times with 20 mL) and was filtered on a Buckner flask. Solids were washed sequentially with water and ether, which was further purified by recrystallization to yield the pure product (157 mg).

$^1$H NMR (300 MHz, CDCl$_3$): δ 5.77 (d, J=6 Hz, 2H), 3.60-3.75 (m, 2H), 3.02-3.13 (m, 2H), 2.05-2.15 (m, 2H), 1.85-1.95 (m, 2H), 1.55-1.62 (m, 6H), 1.10-1.40 (m, 6H); $^{195}$Pt NMR (64.5 MHz, CDCl$_3$): δ −2240.0.

Cis-bis(cyclopropaneacetonitrile)dichloroplatinum (II) (BNP3014/c)

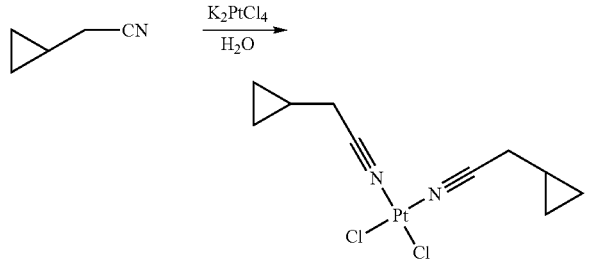

A mixture of potassium tetrachloroplatinate (415 mg, 1.0 mmol) and cyclopropaneacetonitrile (5 mmol) in deionized water was stirred for two days at room temperature. The reaction mixture was extracted with diethyl ether (3-times with 20 mL) and was filtered on a Buckner flask. Solids were washed sequentially with water and ether, which was further purified by recrystallization to yield the pure product (198 mg).

$^1$H-NMR (300 MHz, CDCl$_3$): δ 2.93-2.90 (m, 4H), 1.26-1.14 (m, 2H), 0.76-0.68 (m, 4H), 0.48-0.38 (m, 4H), $^{195}$Pt NMR(64.5 MHz, CDCl$_3$): δ −2273.5.

Trans-bis(4-methoxyphenylpropinonitrile)dichloroplatinum (II) (BNP3034/t)

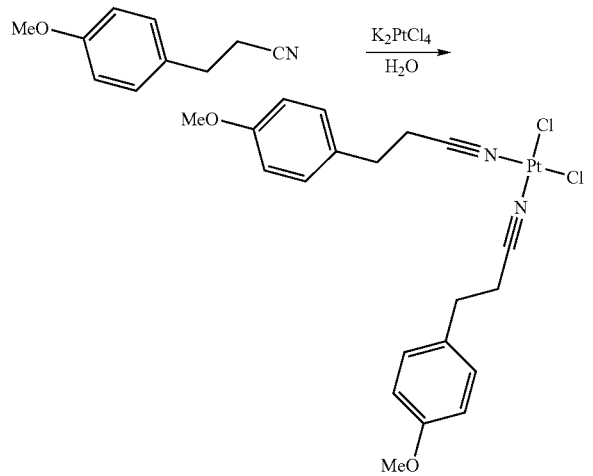

A mixture of potassium tetrachloroplatinate (415 mg, 1.0 mmol) and 3-(4-methoxyphenylpropinonitrile (5 mmol) in deionized water was stirred for 6 hours at 65° C. The reaction mixture was extracted with diethyl ether (3-times with 20 mL) and was filtered on a Buckner flask. Solids were washed sequentially with water and ether, which was further purified by recrystallization to yield the pure product (290 mg).

$^1$H-NMR (300 MHz, CDCl$_3$): δ 7.17 (d, J=8.4 Hz, 4H), 6.89 (d, J=8.4 Hz, 4H), 3.81 (s, 6H), 3.09-2.92 (m, 8H); $^{195}$Pt NMR (64.5 MHz, CDCl$_3$): δ −2340.7.

Cis-bis(3-trifluoroethoxy-propionitrile)dichloroplatinum (II) (BNP3032)

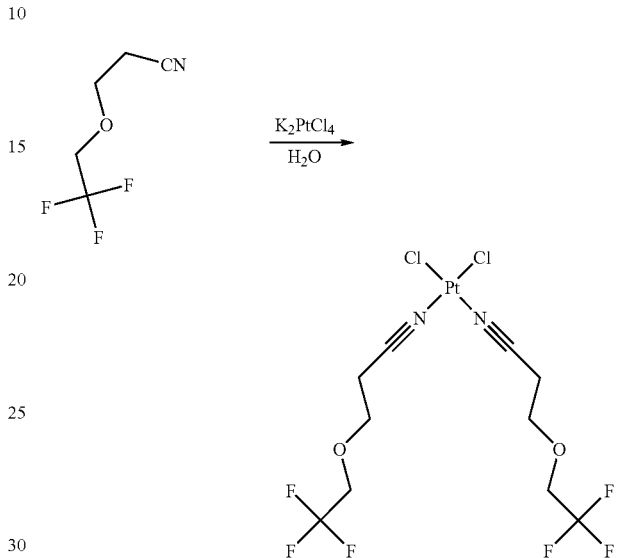

A mixture of potassium tetrachloroplatinate (415 mg, 1.0 mmol) and 3-trifluoroethoxylpropinonitrile (4 mmol) in deionized water was stirred for 5 days at room temperature. The aqueous layer was extracted with methylene chloride (three times). The combined organic layers were dried over sodium sulfate, and concentrated to give a yellow solid, which was further purified by recrystallization to yield the pure product (275 mg).

$^1$H-NMR (300 MHz, CDCl$_3$): δ 3.90-4.10 (m, 8H), 3.22-3.08 (m, 4H); $^{195}$Pt NMR(64.5 MHz, CDCl$_3$): δ −2371.6.

Cis-bis-(4-cyanomethyltetrahydropyran)dichloroplatinum (II) (BNP3027)

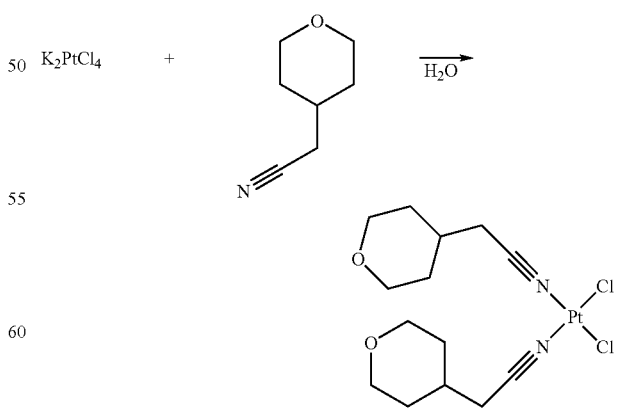

Potassium tetrachloroplatinate (II) (1.00 g, 2.40 mmol) was dissolved in 10 mL of water at room temperature. 4-Cyanomethyl tetrahydropyran (1.20 g, 9.60 mmol) was added to this solution. The reaction was stirred at 50° C. for 4 hours. The solvent was removed under vacuum. The residual solid was washed with ethyl ether, then extracted with in dichloromethane and dried under vacuum. Yellow precipitate was filtered, washed with ethyl ether, and dried under vacuum. The designed product (0.246 g) was obtained.

[195]Pt-NMR (64.5 MHz, acetone-d): δ −1994.6; MS (M[+]+Na): 539.31.

Trans-bis-[2-(trifluoromethyl)-phenylacetonitrile] dichloroplatinum (BNP3037/t)

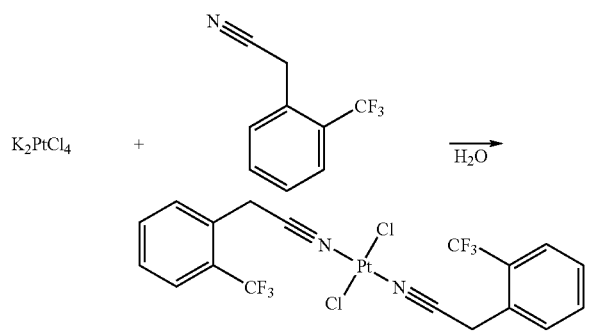

Potassium tetrachloroplatinate (II) (500 mg, 1.20 mmol) was dissolved in 10 mL of water at room temperature. To this was added 2-(trifluoromethyl)-phenylacetonitrile (889 mg, 2.40 mmol). The reaction was stirred at 50° C. for 5 days. The solvent was removed under vacuum. The residual solid was washed with ethyl ether, then extracted with dichloromethane, and dried under vacuum. The yellow solid was dissolved in dichloromethane and kept in the refrigerator. The yellow crystals were filtered and dried. The desired product was obtained 249 mg (36%).

$^1$H-NMR (300 MHz, CDCl$_3$): δ 7.75-7.52 (m, 8H), 4.43 (d, J=20.7 Hz, 4H); [195]Pt-NMR (64.5 MHz, CDCl$_3$): δ −2377.7.

Cis-bis-[4-(trifluoromethoxy)-phenylacetonitrile] dichloroplatinum (II) (BNP3031)

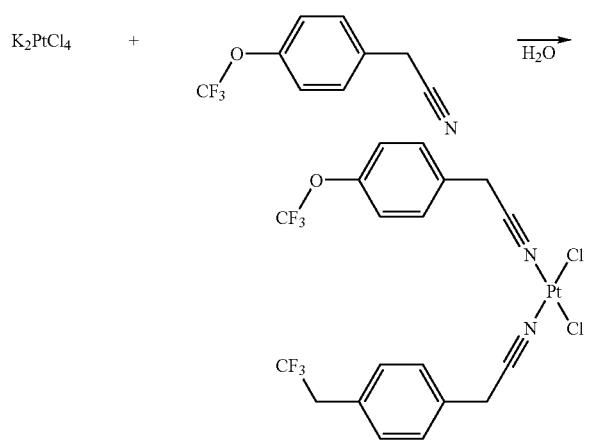

Potassium tetrachloroplatinate (II) (500 mg, 1.20 mmol) was dissolved in 10 mL of water at room temperature. To this was added 4-(trifluoromethoxy)-phenylacetonitrile (966 mg, 2.40 mmol). The reaction was stirred at 50° C. for 1 day. The solvent was removed under vacuum. The residual solid was washed with ethyl ether, then extracted with dichloromethane and dried under vacuum. The yellow solid was dissolved in dichloromethane and kept in the refrigerator. The yellow crystals were filtered and dried. The desired product (230 mg) was obtained.

$^1$H-NMR (300 MHz, CDCl$_3$): δ 7.37 (d, J=9.0 Hz, 4H), 7.23 (d, J=8.4 Hz, 4H), 4.20 (s, 4H); [195]Pt-NMR (64.5 MHz, CDCl$_3$): δ −2281.9.

Cis-bis-(4-phenylbutyronitrile)dichloroplatinum (II), BNP3029/c

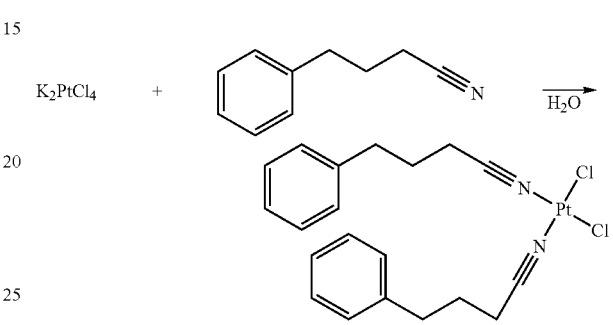

Potassium tetrachloroplatinate (II) (1.00 g, 2.40 mmol) was dissolved in 15 mL of water at room temperature. To this was added 4-phenylbutyronitrile (1.40 g, 9.64 mmol). The reaction was stirred at 50° C. for 1 day. The solvent was removed under vacuum. The residual solid was washed with ethyl ether, then extracted with dichloromethane and dried under vacuum. The yellow solid was dissolved in dichloromethane and kept in the refrigerator. The brown crystals were filtered and dried. The designed product (286 mg) was obtained.

$^1$H-NMR (300 MHz, CDCl$_3$): δ 7.31-7.15 (m, 10H), 2.83-2.74 (m, 8H), 2.13-2.03 (m, 4H); [195]Pt-NMR(64.5 MHz, CDCl$_3$): δ −2262.5.

Trans-bis-(4-phenylbutyronitrile)dichloroplatinum (II) (BNP3027)

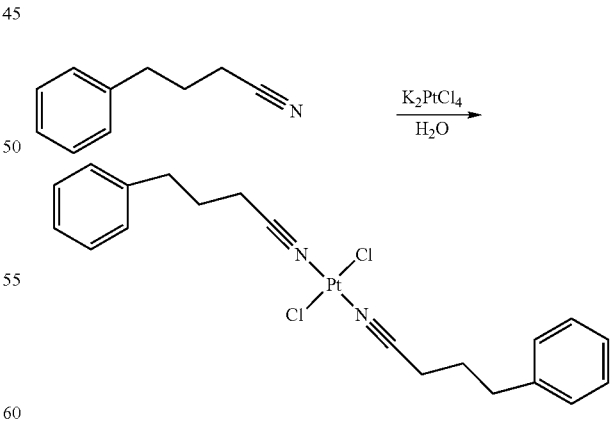

Potassium tetrachloroplatinate (II) (500 mg, 1.20 mmol) was dissolved in 10 mL of water at room temperature. To this was added 4-Phenyl butyronitrile (697 mg, 4.80 mmol). The reaction was stirred at 50° C. for 5 day. The solvent was removed under vacuum. The residual solid was washed with diethyl ether, then extracted with in dichloromethane and dried under vacuum. The yellow solid was dissolved in dichloromethane, and kept in the refrigerator. The brown crystals were filtered, and dried. The designed product (286 mg) was obtained.

$^1$H-NMR(300 MHz, CDCl$_3$): δ 7.31-7.16 (m, 10H), 2.79-2.69 (m, 8H), 2.04-1.97 (m, 4H); $^{195}$Pt-NMR(64.5 MHz, CDCl$_3$): δ −2336.4.

Cis-bis-(cyclobutanecarbonitrile)dichloroplatinum (II) (BNP3021)

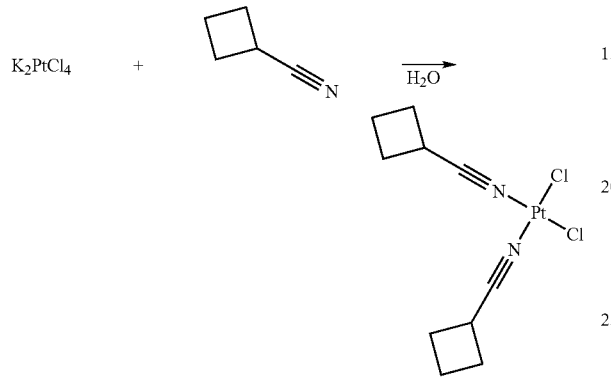

Potassium tetrachloroplatinate (II) (500 mg, 1.20 mmol) was dissolved in 10 mL of water at room temperature. To this was added cyclobutanecarbonitrile (390 mg, 4.80 mmol), and stirred at room temperature for 2 days. The solvent was removed under vacuum. The residual solid was washed with ethyl ether, then extracted with dichloromethane and dried under vacuum. The crude was further purified by recrystallization to yield the pure product (337 mg).

$^1$H-NMR(300 MHz, CDCl$_3$): δ 3.69-3.58 (m, 2H), 2.57-2.41 (m, 8H), 2.24-2.00 (m, 4H); $^{195}$Pt-NMR(64.5 MHz, CDCl$_3$): δ −2268.8.

Cis-bis(3-furonitrile)dichloroplatinum (II) (BNP2507)

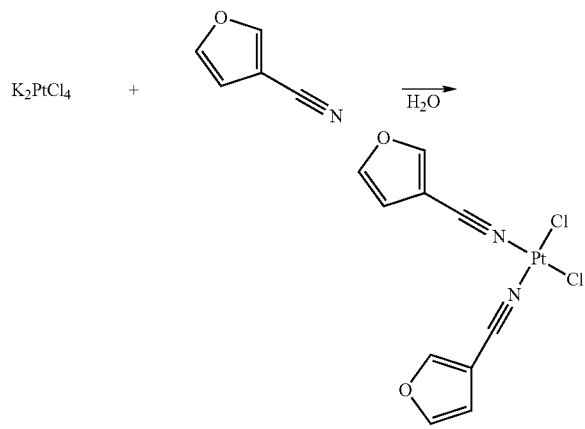

A mixture of potassium tetrachloroplatinate (1.0 g, 2.4 mmol) and 3-furonitrile (1.0 g, 10.7 mmol) in deionized water (8 mL) and diethyl ether (2 mL) was stirred at room temperature for 28 hours. The resulting suspension was filtered. The solid was washed with water and diethyl ether, and dried under vacuum. The dried solid was extracted with methylene chloride (3-times with 10 mL). The combined extracts were concentrated to about 5 mL under reduced pressure. The precipitated solid was filtered, washed with methylene chloride (1 mL) and dried under vacuum to give 138 mg of pure product as a yellow solid.

$^1$H NMR (300 MHz, DMF-d$_7$):δ 7.03 (dd, J$_1$=1.95, J$_2$=0.75 Hz, 2H), 7.86 (t, J=1.8 Hz, 2H), 8.80 (t, J=0.75 Hz, 2H); $^{195}$Pt NMR (64.5 MHz, DMF-d$_7$)δ: −2260.2.

Cis-bis(3,4-(methylenedioxy)phenylacetonitrile) dichloroplatinum (II) (BNP3016)

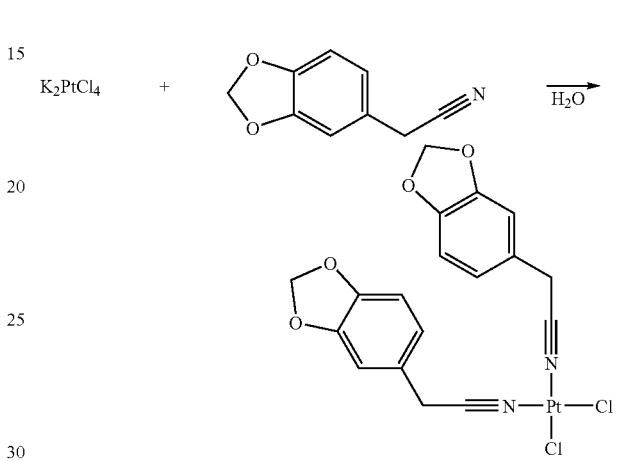

A mixture of potassium tetrachloroplatinate (500 mg, 1.2 mmol) and 3,4-(methylenedioxy)phenylacetonitrile (600 mg, 3.7 mmol) in deionized water (10 mL) was stirred at room temperature for 7 days. The resulting suspension was filtered and the solid was stirred in a mixture of water (10 mL) and diethyl ether (15 mL) for 15 minutes. The solid was filtered and washed with fresh water and diethyl ether. It was then stirred in methylene chloride (15 mL) for 20 minutes, filtered, washed with fresh methylene chloride and dried under vacuum to give 230 mg of pure product as a light yellow solid.

$^1$H NMR (300 MHz, DMF-d$_7$): δ 4.60 (s, 2H), 6.12 (s, 2H), 6.948 (s, 1H), 6.951 (s, 1H), 7.04 (s, 1H); $^{195}$Pt NMR (64.5 MHz, DMF-d$_7$): δ −2265.3.

II. Specific Examples of Experimental Data

The following data, as illustrated in Table 1, shows the results of utilizing the bis-nitrile-containing platinum compounds of the present invention in various cell lines. All experiments are with 1 hour of exposure to the drug, IC$_{50}$ in μM. The platinum compounds have been tested by the resistance factor in CP3 cell line (CP3 Rfact) and C25 cell line (C25 Rfact). The terms (CP3 Rfact) and (C25 Rfact) are determined utilizing the following equations, wherein WT stands for wild-type.

$$CP3\ Rfact = IC_{50}\ in\ A2780/CP3 \div IC_{50}\ in\ A2780/WT$$

$$C25\ Rfact = IC_{50}\ in\ A2780/C25 \div IC_{50}\ in\ A2780/WT$$

Various compounds have been tested multiple times, and the average of the IC$_{50}$ was taken, this number of times the experiment was performed is illustrated in the Column designated "Average of". In addition, Compounds with " - - - " in the IC$_{50}$ column indicate the IC$_{50}$s are >100 μM.

The most promising 8 compounds with resistance factors (Rfact) numbers of <2 in the in CP3 and C25 cell lines are as follows: (1) BNP3030, (2) BNP3020, (3) BNP3031, (4) BNP3029/c, (5) BNP3029/t, (6) BNP3017, (7) BNP3026, (8) BNP3024,

TABLE 1

| BNP# | Ligands | Mol Wt. | IC$_{50}$ in A2780/WT | IC$_{50}$ in A2780/CP3 | CP3 Rfact | IC$_{50}$ in A2780/C25 | C25 Rfact | Average of | Purity |
|---|---|---|---|---|---|---|---|---|---|
| BNP3029/t | (4-phenylbutanenitrile structure) | 556.41 | 16.22 | 19.25 | 1.19 | 17.70 | 1.09 | 3 | 94.2 |
| BNP3030 | (bicyclo[4.2.0]octa-1,3,5-triene-7-carbonitrile structure) | 524.32 | 51.38 | 61.85 | 1.20 | 58.85 | 1.15 | 2 | 95.4 |
| BNP3026 | (2-(m-tolyl)acetonitrile structure) | 528.35 | 21.60 | 28.50 | 1.32 | 23.98 | 1.11 | 2 | 99.3 |
| BNP3017 | (4-methoxy-4-phenylbutanenitrile structure) | 616.46 | 14.03 | 18.75 | 1.34 | 18.05 | 1.29 | 3 | 97.6 |
| BNP3024 | (2-(o-tolyl)acetonitrile structure) | 528.35 | 13.93 | 18.60 | 1.34 | 18.70 | 1.34 | 2 | 99.0 |
| BNP3029/c | (4-phenylbutanenitrile structure) | 556.41 | 4.40 | 6.88 | 1.56 | 5.45 | 1.24 | 2 | 99.9 |

TABLE 1-continued
| BNP# | Ligands | Mol Wt. | IC$_{50}$ in A2780/WT | IC$_{50}$ in A2780/CP3 | CP3 Rfact | IC$_{50}$ in A2780/C25 | C25 Rfact | Average of | Purity |
|---|---|---|---|---|---|---|---|---|---|
| BNP3020 | 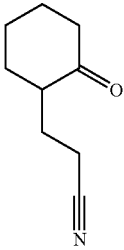 | 568.40 | 51.60 | 84.3 | 1.63 | 61.55 | 1.19 | 1 | 98.7 |
| BNP3031 | 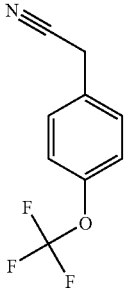 | 668.29 | 18.43 | 35.88 | 1.95 | 23.23 | 1.26 | 2 | 99.9 |
| BNP3036/t |  | 601.02 | 23.70 | 54.15 | 2.28 | 35.25 | 1.49 | 1 | 99.3 |
| BNP3034/t | 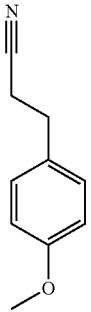 | 588.41 | 17.55 | 41.15 | 2.34 | 28.05 | 1.60 | 1 | 99.1 |
| BNP3014/c | 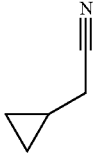 | 430.25 | 23.33 | 55.67 | 2.39 | 45.35 | 1.94 | 3 | 98.9 |

TABLE 1-continued

| BNP# | Ligands | Mol Wt. | IC$_{50}$ in A2780/WT | IC$_{50}$ in A2780/CP3 | CP3 Rfact | IC$_{50}$ in A2780/C25 | C25 Rfact | Average of | Purity |
|---|---|---|---|---|---|---|---|---|---|
| BNP3034/c | 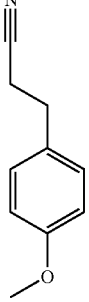 | 588.41 | 18.35 | 44.50 | 2.43 | 28.10 | 1.53 | 1 | 99.9 |
| BNP3021 | 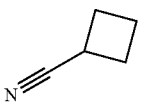 | 428.23 | 13.90 | 41.30 | 2.97 | 29.2 | 2.10 | 1 | 93.4 |
| BNP3037/t |  | 636.30 | 87.10 | — | — | 68.70 | 0.79 | 1 | 99.6 |
| BNP3022 | 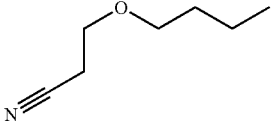 | 520.37 | 73.75 | — | — | 65.00 | 0.88 | 1 | 97.0 |
| BNP3014/t |  | 430.25 | 68.10 | — | — | 91.95 | 1.35 | 1 | 93.1 |
| BNP3016 | 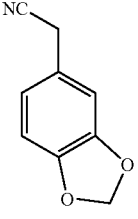 | 588.31 | 62.40 | 75.60 | 1.21 | 66.50 | 1.07 | 2* | 87.1 |

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A bis-nitrile platinum analog selected from the group consisting of: Cis-(3-[2-(2-cyano-ethoxy)-ethoxy]-propionitrile)dichloroplatinum (II) (BNP 3015); Cis-bis(3-methoxy-propionitrile)dichloroplatinum (II) (BNP 2509); Cis-bis(morpholine-4-carbonitrile)dichloroplatinum (II) (BNP3019); Cis-bis[3-(2-oxo-cyclohexyl)-propionitrile]dichloroplatinum (II) (BNP3020); Cis-bis[(3-fluoro-phenyl)-acetonitrile]dichloroplatinum (II) (BNP3028); Cis-bis(bicyclo[4.2.0]octa-1(6),2,4-triene-7-carbonitrile)dichloroplatinum (II) (BNP3030); Cis-bis[(3,4-diethoxyphenyl)acetonitrile]dichloroplatinum (II) (BNP3035); Trans-bis(2,6-difluoro-3-methylphenylacetonitrile)dichloroplatinum (II) (BNP3036/t); Cis-bis(4-methoxy-4-phenylbutyronitrile)dichloroplatinum (II) (BNP3017); Cis-bis[2-(difluoromethoxy)phenylacetonitrile]dichloroplatinum (II) (BNP3038); Cis-bis(4-methyl-4-nitro-veleronitrile) dichloroplatinum (II) (BNP3018); Cis-bis(3-butoxypropanenitrile)dichloroplatinum (II) (BNP3022); Trans-bis(cyclopropaneacetonitrile)dichloroplatinum (II) (BNP3014/t); Cis-bis(2-hydroxycyclohexanecarbonitrile)dichloroplatinum (II) (BNP3013); Cis-bis(cyclopropaneacetonitrile)dichloroplatinum (II) (BNP3014/c); Trans-bis(4-methoxyphenylpropiononitrile)dichloroplatinum (II) (BNP3034/t); Cis-bis(3-trifluoroethoxy-propionitrile)dichloroplatinum (II) (BNP3032); Cis-bis-(4-cyanomethyltetrahydropyran) dichloroplatinum (II) (BNP3027); Trans-bis-[2-(trifluoromethyl)-phenylacetonitrile]dichloroplatinum (BNP3037/t); Cis-bis-[4-(trifluoromethoxy)-phenylacetonitrile)]dichloroplatinum (II) (BNP3031); Cis-bis-(4-phenylbutyronitrile)dichloroplatinum (II), BNP3029/c); Trans-bis-(4-phenylbutyronitrile)dichloroplatinum (II) (BNP3027); Cis-bis-(cyclobutanecarbonitrile)dichloroplatinum (II) (BNP3021); Cis-bis(3-furonitrile)dichloroplatinum (II) (BNP2507); Cis-bis(3,4-(methylenedioxy)phenylacetonitrile)dichloroplatinum (II) (BNP3016); and pharmaceutically-acceptable salts thereof.

2. A bis-nitrile platinum analog having the following structural formula:

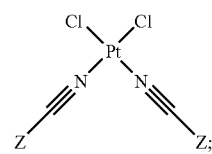

wherein both Z substituent groups are identical and are selected from the group consisting of: 3-[2-(2-cyano-ethoxy)-ethoxy]-propionitrile; 3-methoxy-propionitrile; morpholine-4-carbonitrile; (3-fluoro-phenyl)-acetonitrile; bicyclo[4.2.0]octa-1(6),2,4-triene-7-carbonitrile; (3,4-diethoxy-phenyl)acetonitrile; 2,6-difluoro-3-methylphenylacetonitrile; 4-methoxy-4-phenylbutyronitrile; 2-(difluoromethoxy) phenylacetonitrile; 4-methyl-4 nitro-veleronitrile; 3-butoxypropanenitrile; cyclopropaneacetonitrile; 4-methoxyphenylpropionitrile; 3-trifluoroethoxy-propionitrile; 4-cyanomethyltetrahydropyran; 2-(trifluoromethyl)-phenylacetonitrile; 4-(trifluoromethoxy)-phenylacetonitrile; 4-phenylbutyronitrile; cyclobutanecarbonitrile 3-[2-(2-cyano-ethoxy)-ethoxy]-propionitrile; cis-(3-furonitrile); or cis-(3,4-(methylenedioxy)) phenylacetonitrile.

3. A composition comprising a pharmaceutically-effective amount of an anti-cancer bis-nitrile platinum analog of claim 1 or claim 2 admixed with one or more pharmaceutically-acceptable carriers.

4. A method of treating cancer, said method comprising administering to a patient in need thereof a pharmaceutically-effective amount of the composition of claim 3.

* * * * *